United States Patent [19]
Jacob

[11] Patent Number: 6,077,073
[45] Date of Patent: Jun. 20, 2000

[54] LIGHT EMITTING DIODE-ARRAY LIGHT APPARATUS

[76] Inventor: Gregory S. Jacob, 9672 Reding Cir., Des Plaines, Ill. 60016

[21] Appl. No.: 09/153,653

[22] Filed: Sep. 15, 1998

[51] Int. Cl.[7] ..................................................... A61C 1/00
[52] U.S. Cl. ................................................................. 433/29
[58] Field of Search ................................. 433/29; 606/13, 606/14, 17; 600/241, 245, 249

[56] References Cited

U.S. PATENT DOCUMENTS

| | | | |
|---|---|---|---|
| 936,499 | 10/1909 | Werner | 600/245 |
| 1,533,605 | 4/1925 | Pelton et al. | 600/245 |
| 2,296,793 | 9/1942 | Kirschbaum | 600/245 |
| 2,528,458 | 10/1950 | Stone | 600/245 |
| 2,800,896 | 7/1957 | Thum | 600/245 |
| 4,807,599 | 2/1989 | Robinson et al. | 433/299 |
| 5,201,655 | 4/1993 | Friedman . | |
| 5,290,169 | 3/1994 | Friedman et al. . | |
| 5,316,473 | 5/1994 | Hare . | |
| 5,328,368 | 7/1994 | Lansing et al. | 433/29 |
| 5,415,543 | 5/1995 | Rozmajzl, Jr . | |
| 5,487,662 | 1/1996 | Kipke et al. . | |
| 5,634,711 | 6/1997 | Kennedy et al. . | |
| 5,702,250 | 12/1997 | Kipke et al. . | |
| 5,711,665 | 1/1998 | Adam et al. . | |
| 5,718,577 | 2/1998 | Oxman et al. . | |
| 5,782,896 | 7/1998 | Chen et al. | 606/14 |
| 5,865,621 | 2/1999 | Calderwood | 433/29 |
| 5,893,712 | 4/1999 | Stone et al. | 433/29 |

*Primary Examiner*—Todd E. Manahan
*Attorney, Agent, or Firm*—Pauley Petersen Kinne & Fejer

[57] ABSTRACT

A sheathed, conformable, multi-tooth device for curing adhesives, sealants and/or whitening or coloring agents used in the dentistry field is disclosed. An array of LED lights are connected and a relatively low voltage (e.g., 5 volts) powers the LED array. The LED array is housed within a clear, transparent and/or translucent housing constructed of either a solid, such as a poured resin, or a hollow structure. The housing conforms to an approximate shape of dentition. The housing is mountable within a disposable oversertion sheath. During use, the LED array transmits light which cures the adhesives, sealants and/or whitening or coloring agents, preferably on several teeth simultaneously.

5 Claims, 8 Drawing Sheets

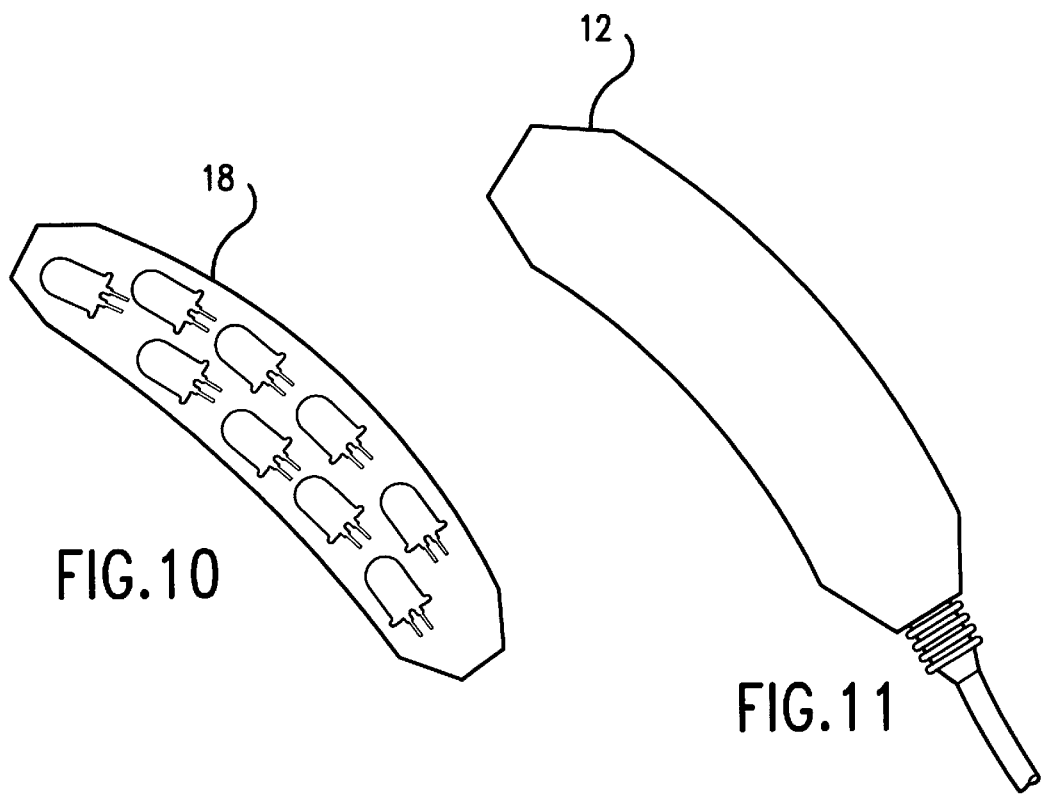
FIG.10
FIG.11
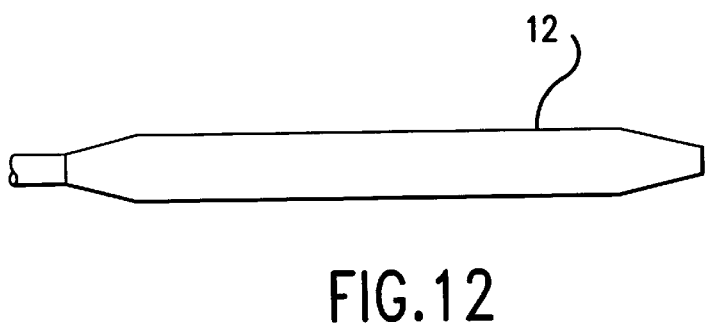
FIG.12

LIGHT EMITTING DIODE-ARRAY LIGHT APPARATUS

BACKGROUND OF THE INVENTION

1. Field of the Invention

This invention relates to a sheathed, conformable, multi-tooth light emitting diode-array light apparatus for curing adhesives, sealants and/or whitening or coloring agents used in the dentistry field.

2. Description of Prior Art

U.S. Pat. No. 5,201,655, issued to Friedman on Apr. 13, 1993 and entitled "Optical Light Guide for Controlling the Iradiation of a Dental Restorative Material," teaches a light guide adapted for photocuring. Two optical conductors are spaced to form a gap adapted to receive a tooth. This apparatus, as disclosed, is quite bulky in design and rather frightening in appearance, especially for use in children. Furthermore, it is only adaptable to working on one tooth at a time, and hence lacks the convenience and function of a conformable multi-tooth apparatus. Additionally, without the provision of a protective barrier interposed between the apparatus and the tooth, the device is unsanitary.

U.S. Pat. No. 5,290,169, issued to Friedman, et al. on March 01, 1994 and entitled "Optical Light Guide for Dental Light-Curing Lamps," discloses an optical light guide constructed of a transparent material, such as glass, acrylic, polystyrene and/or polycarbonate. FIG. 2 of the '169 patent shows how light is reflected within the light guide and directed at a tooth not using direct exposure of the light source at the treatment site. This device, too, is quite bulky in design. The device further is only adaptable to working on one tooth at a time, and hence lacks the convenience and function of a conformable multi-tooth apparatus. Additionally, without the provision of a protective barrier interposed between the apparatus and the tooth, the device is unsanitary.

U.S. Pat. No. 5,316,473, issued to Hare on May 31, 1994 and entitled "Light Curing Apparatus and Method," discloses a light-curing apparatus including a dental tray and a wand which either fits over the dental tray or is slidably engaged with the dental tray. FIGS. 2 and 3 of the '473 patent show the wand having a plurality of light sources 15, which may be a series of light bulbs or a series of light emitting diodes (FIG. 2), or which may be fiber optic element 20 having optic fibers 28 with ends 24 that emit light into an impression material. This device suffers the drawback that it relies on fiber optic light, and hence is more costly than other devices. Additionally, the apparatus is not conformable to any shape mouth or for working in conjunction with the upper and lower teeth at the same time. Moreover, without the provision of a protective barrier interposed between the apparatus and the tooth, the device is unsanitary. Furthermore, a multitude of tray and wand sizes must be manufactured to fit different mouths, making the apparatus complicated and expensive.

U.S. Pat. No. 5,415,543, issued to Rozmajzl, Jr. on May 16, 1995 and entitled "Dental Composite Curing Apparatus and Method," teaches a dental apparatus for curing actinic light curable composites, primers and adhesives. As shown in FIG. 2 of the '543 patent, nozzle 62 is centered within fiber optics tube 128, which is housed within annular conduit 150. A plurality of bores or orifices 152 are distributed about fiber optic tube 128. Gas flows out of the bores or orifices to form a uniform blanket of inert gas adjacent an emitting end of the apparatus. As shown in FIG. 1, actinic light source 20 is a visible, ultraviolet, infrared or laser light source, depending upon the type of adhesive, primer or composite to be cured. This device also suffers the drawback that it relies on fiber optic light, and hence is more costly than other devices. Additionally, the apparatus is not adaptable to working with more than one tooth at a time and is not conformable to any shape mouth for working in conjunction with more than one tooth at a time. Furthermore, without the provision of a protective barrier interposed between the apparatus and the tooth, the device is unsanitary. This device involves the use of sealed, inert gases, not solid state electro-optics. Thus, loss or leakage of the gases may occur over time.

U.S. Pat. No. 5,487,662, issued to Kipke, et al. on Jan. 30, 1996 and entitled "Dental Impression Tray for Photocurable Impression Material," teaches a dental impression tray for photocurable impression material. A light source, such as a solid state light emitter or a light emitting diode, is contained within the dental impression tray. As shown in FIG. 1, emitters 18 are positioned at spaced intervals over body 12 of the dental impression tray. FIGS. 3 and 4 of the '662 patent show different positions of emitters 18. FIG. 5 of the '662 patent shows a bank of emitters 164, such as light emitting diodes, which are used to provide light to emitters 18. This device has as a serious shortcoming no protective barrier interposed between the apparatus and the tooth. Hence, the device is unsanitary. Additionally, the apparatus is not conformable to any shape mouth for working in conjunction with both the upper and lower teeth at the same time. A variety of sizes must be manufactured to accommodate different mouth sizes.

U.S. Pat. No. 5,634,711, issued to Kennedy, et al. on Jun. 03, 1997 and entitled "Portable Light Emitting Apparatus with a Semiconductor Emitter Array," teaches a hand-held portable light emitting device for photocuring and phototherapy applications. A matrix of light emitting diodes are mounted at a front end of a housing, and emit light energy which is suitable for initiating a photo-reaction. This device, too, is quite bulky in design. Additionally, the apparatus is not adaptable to working with more than one tooth at a time and is not conformable to any shape mouth for working in conjunction with more than one tooth at a time. Also, without the provision of a protective barrier interposed between the apparatus and the tooth, the device is unsanitary. This device further requires cooling air.

U.S. Pat. No. 5,702,250, issued to Kipke on Dec. 30, 1997 and entitled "Compact Dental Impression Tray for Photocurable Impression Material," discloses a dental impression tray that has an array of solid state light emitters for curing photocurable impression material received in a channel of the tray. As shown in FIG. 2 of the '250 patent, emitters 32, such as light emitting diodes, are positioned to emit light to the impression material. This device has as a serious shortcoming no protective barrier interposed between the apparatus and the tooth. Hence, the device is unsanitary. Additionally, the apparatus is not conformable to any shape mouth for working in conjunction with more than one tooth at a time, and does not permit light exposure simultaneously to the right and left sides of the mouth.

U.S. Pat. No. 5,711,665, issued to Adam, et al. on Jan. 27, 1998 and entitled "Method and Apparatus for Binding Orthodontic Brackets to Teeth," teaches a method and a device to bond orthodontic brackets to teeth. A curing light is removably received within a passage of the bracket. This device is quite bulky in design and has no protective barrier interposed between the apparatus and the tooth. Designed more for use with braces, the device is unsanitary insomuch as repeated, direct contact between the device and the mouth is expected. Additionally, the apparatus is not conformable to any shape mouth for working in conjunction with more than one tooth at a time. The key/keyhole design and use makes the method difficult to employ, requiring laborious skill in placement for each tooth.

U.S. Pat. No. 5,718,577, issued to Oxman, et al. on Feb. 17, 1998 and entitled "Dental Impression Tray with Chemiluminescent Light Source," teaches a dental impression tray that forms a channel which receives or contains a photocurable dental impression material. A wall or a wall portion adjacent the chamber is constructed of a material that transmits electromagnetic actinic radiation. Another chamber of the tray contains a chemiluminescent composition that cures the photocurable dental impression material. The device relies on a chemical reaction to produce the light used during the cure instead of direct illumination with solid state electro-optics. Additionally, the apparatus is not conformable to any shape mouth; hence, different sizes must be manufactured to accommodate a variety of mouth sizes. Furthermore, the device is most adaptable for working in conjunction with one tooth at a time; it cannot be accommodated to work on both the upper and lower teeth simultaneously. Furthermore, without the provision of a protective barrier interposed between the apparatus and the tooth, the device is unsanitary.

Thus, a problem associated with light curing apparatus for use in dentistry that precede the present invention is that many of them are bulky in design, and hence cumbersome to use.

Yet another problem associated with light curing apparatus for use in dentistry that precede the present invention is that many of them are hand-held, and hence difficult to use with precision. The dental operator, an assistant or the patient himself may be required to stabilize the apparatus during its entire placement time in the patient's mouth.

Still a further problem associated with light curing apparatus for use in dentistry that precede the present invention is that many of them are only adaptable to working on one tooth at a time, and hence do not facilitate rapid working conditions during dentistry. Certainly, none known to Applicant accommodates working on both (1) the upper and lower teeth at the same time and (2) the left and right sides of the mouth at the same time.

Yet an additional problem associated with light curing apparatus for use in dentistry that precede the present invention is that many of them are frightening in appearance, and hence susceptible to consumer rejection. Children, especially, may be averse to bulky equipment.

Another problem associated with light curing apparatus for use in dentistry that precede the present invention is that many of them are chemically activated, in that many of them rely on light produced from a chemical reaction for their efficacy. Calibration of this equipment may be needed to correct for leakage or depletion of gases over time.

Still a further problem associated with light curing apparatus for use in dentistry that precede the present invention is that many of them are expensive to manufacture and use, particularly where a multiplicity of sizes is required.

Yet an additional problem associated with light curing apparatus for use in dentistry that precede the present invention is that many of them must be reused in their entirety to be cost effective. Where a multiplicity of sizes is required, the dental office is faced with the prospect of stocking many such apparatus, concomitantly driving up the cost of using such apparatus.

Still a further problem associated with light curing apparatus for use in dentistry that precede the present invention is that many of them rely on fiber optic light, and hence are perhaps more costly than other devices. These are not self-contained in a small package. Furthermore, these may even generate harmful levels of heat at the light source, requiring indirect illumination.

Yet an additional problem associated with light curing apparatus for use in dentistry that precede the present invention is that many of them are designed essentially for use with dental braces or brackets.

Another problem associated with light curing apparatus for use in dentistry that precede the present invention is that they lack the appearance of being sanitary, and hence are even more susceptible to consumer rejection and may contribute to the spread of infection by cross-contamination. Additionally, their design does not permit ease of total sanitation of all parts, particularly those that are difficult to access during the sanitation process.

An even further problem associated with light curing apparatus for use in dentistry that precede the present invention is that they are not conformable to any shape mouth for working in conjunction with the upper and the lower teeth at the same time.

For the foregoing reasons, there has been defined a long felt and unsolved need for a light curing apparatus for use in dentistry that is sterile in fact, sanitary in appearance and hence perceived to be sterile, easily placed in the mouth, inexpensive to manufacture and adjustable to accommodate a variety of differently shaped mouths and bites such that a single design can be accommodated to all persons to which it is adapted. Such a device should be self-contained with minimal parts. It should be able to be used to treat as many teeth as maximally possible at the same time, thereby reducing overall treatment time, complexity and expense.

In contrast to the foregoing, the present invention constitutes a light curing apparatus for use in dentistry that seeks to overcome the problems discussed above, while at the same time providing a simple, easily constructed apparatus that is readily adapted to a variety of applications.

SUMMARY OF THE INVENTION

A device for curing adhesives, sealants and/or whitening or coloring agents used in the dentistry field. In one preferred embodiment of this invention, an array of LED (light emitting diode) lights are connected, preferably but not necessarily in parallel. A relatively low voltage source, such as one having less than about 5 volts, delivered from a transformer or battery, preferably powers the LED array. The LED array can be housed within a clear, a transparent and/or a translucent housing. The housing is constructed of a material that may have optical qualities to enhance the LED performance. The housing is preferably sealed. The housing can be constructed of a solid, such as a poured resin, or can be constructed as a hollow structure. The housing preferably has a shape with an overall curve that conforms to an approximate shape of dentition. The housing can also be constructed as a flexible material, including a flexible material that has shape memory characteristics. The housing can be mounted within a disposable oversertion sheath, for sterility purposes. During use, the LED array transmits light which cures the adhesives, sealants and/or whitening or coloring agents, preferably but not necessarily on several teeth simultaneously.

Apparatus of the prior art generally can be bulky and frightening in appearance, leading to consumer rejection. Additionally, these can be unsanitary for multiple use. Many of these apparatus are not adaptable for use in more than one patient. Impression trays of prior patients must be processed for dental casts after removal from the mouth, limiting use to once per placement. Unlike these apparatus, the present invention is therefore compact in design, sanitary for multiple use, and adaptable for use in more than one patient. Impression trays of prior patients need not be processed for dental casts after removal from the mouth, thus permitting more than one use per placement. The apparatus can be use to cure or expose light to several different teeth simultaneously, including upper, lower, right and left sides if maintained across the dentition to transverse the tongue.

It is therefore an object of the present invention to provide a conformable, multi-tooth light emitting diode-array light apparatus for curing adhesives, sealants and/or whitening or coloring agents used in the dentistry field that is not bulky in design.

Still another object of the present invention is to provide a conformable, multi-tooth light emitting diode-array light apparatus for curing adhesives, sealants and/or whitening or coloring agents used in the dentistry field that is not hand-held or rigidly stabilized during use.

Yet another object of the present invention is to provide a conformable, multi-tooth light emitting diode-array light apparatus for curing adhesives, sealants and/or whitening or coloring agents used in the dentistry field that is adaptable to working on more than one tooth at a time in the same jaw or in opposing jaws simultaneously.

It is a further object of the present invention to provide a conformable, multi-tooth light emitting diode-array light apparatus for curing adhesives, sealants and/or whitening or coloring agents used in the dentistry field that has a patient-friendly, non-invasive appearance.

Still another object of the present invention is to provide a conformable, multi-tooth light emitting diode-array light apparatus for curing adhesives, sealants and/or whitening or coloring agents used in the dentistry field that is not chemically activated.

Yet another object of the present invention is to provide a conformable, multi-tooth light emitting diode-array light apparatus for curing adhesives, sealants and/or whitening or coloring agents used in the dentistry field that is inexpensive to manufacture and use.

Another object of the present invention is to provide a conformable, multi-tooth light emitting diode-array light apparatus for curing adhesives, sealants and/or whitening or coloring agents used in the dentistry field that is largely reusable while yet preserving its sterility.

Still a further object of the present invention is to provide a conformable, multi-tooth light emitting diode-array light apparatus for curing adhesives, sealants and/or whitening or coloring agents used in the dentistry field that does not rely on fiber optic light.

Yet another object of the present invention is to provide a conformable, multi-tooth light emitting diode-array light apparatus for curing adhesives, sealants and/or whitening or coloring agents used in the dentistry field that is not designed essentially for braces or brackets, but rather is designed for specific applications located on many teeth at the same time.

An even further object of the present invention is to provide a conformable, multi-tooth light emitting diode-array light apparatus for curing adhesives, sealants and/or whitening or coloring agents used in the dentistry field that is sanitary and also conveys the appearance of being sanitary.

Still a further object of this invention is to provide a conformable, multi-tooth light emitting diode-array light apparatus for curing adhesives, sealants and/or whitening or coloring agents used in the dentistry field that is conformable to any shape mouth for working in conjunction with more than one tooth at a time.

These and other objects, advantages and features of the present invention will be apparent from the detailed description that follows.

DESCRIPTION OF THE DRAWINGS

In the detailed description that follows, reference will be made to the following figures:

FIG. 10 illustrates an upper, perspective view of a portion of a preferred embodiment of the apparatus.

FIG. 11 illustrates an upper, perspective view of a portion of a preferred embodiment of the apparatus.

FIG. 12 illustrates a side view of a preferred embodiment of the apparatus shown in FIG. 11.

DETAILED DESCRIPTION OF THE PREFERRED EMBODIMENTS

Figure 1:
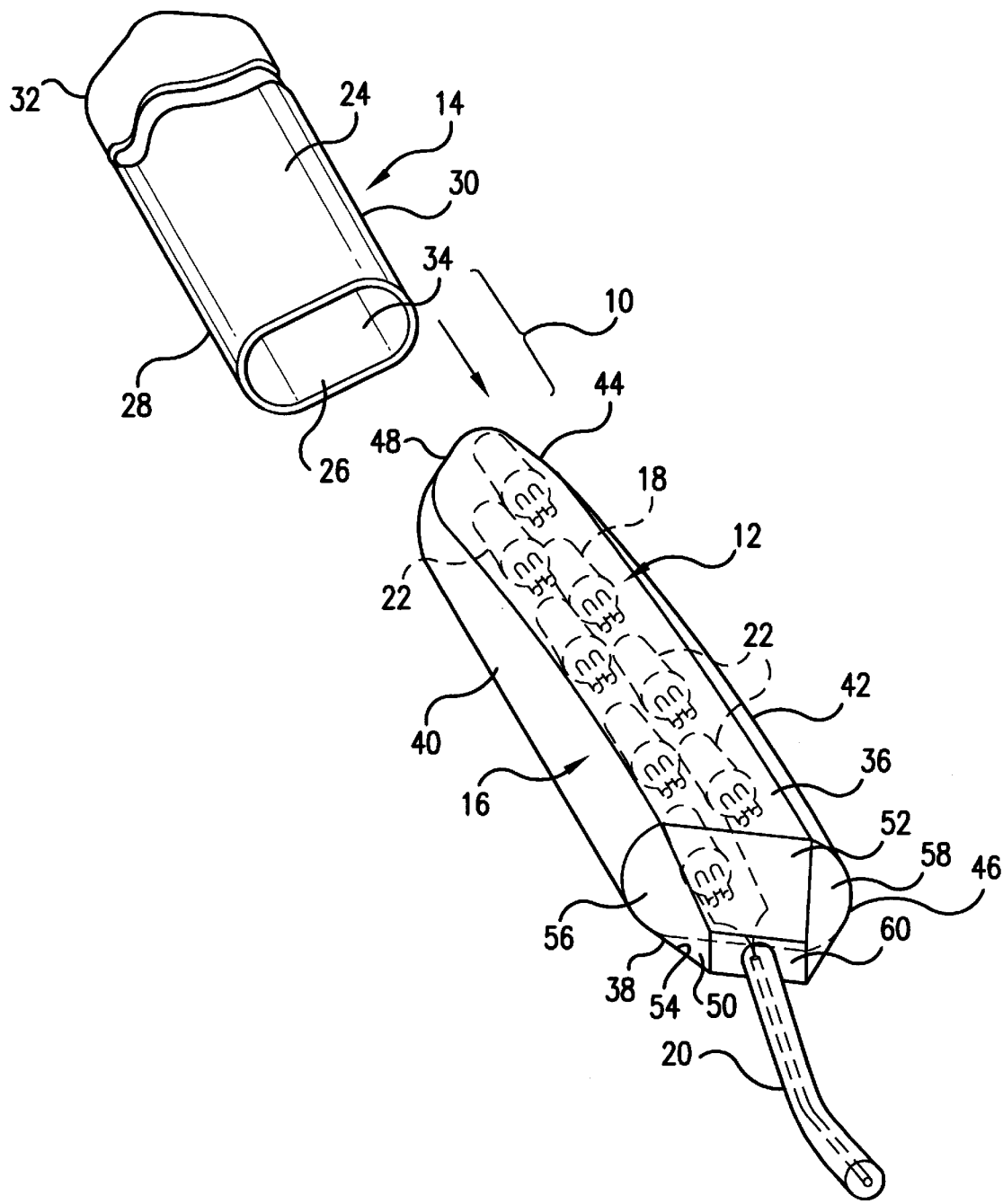
FIG. 1 illustrates an upper, perspective view illustrating a preferred embodiment of the light emitting diode-array light apparatus for curing adhesives, sealants and/or whitening or coloring agents used in the dentistry field.

FIG. 1 illustrates a first embodiment of the conformable, multi-tooth dental curing apparatus 10 constructed and arranged to be received in a human mouth. As constructed, the conformable, multi-tooth curing apparatus 10 comprises a reusable curing section 12 and a disposable sanitary oversertion sheath 14. The curing section 12 has a housing 16 and a LED array 18 contained within the housing 16 so as to be maintained in non-contacting relation with the human mouth. A power supply 20 (to transformer or battery supply, not shown) provides power to individual LED's 22 that are arranged to make up the LED array 18.

Thus, as illustrated, the curing section 12 is reusable, and has an overall length of more than about one inch. The housing 16 has a generally flattened, elongated shape. The oversertion sheath 14 is disposable and also has a generally flattened, elongated shape. Thus, the oversertion sheath 14 is constructed and arranged so as to receive the housing 16, and the housing 16 is likewise constructed and arranged so as to be insertable into the oversertion sheath 14.

Referring now in more detail to the construction of the sanitary oversertion sheath 14, a flat sheath top 24 and a flat sheath bottom 26 are joined by opposed, semicylindrical sheath sides 28, 30 to form a generally flattened tubular shape constructed and arranged to receive the curing section 12. A tapered sheath end 32 defines one end of the housing 16, and a housing receiving aperture 34 is provided at the opposite end. The sanitary oversertion sheath 14 is preferably constructed of a deformable, resilient plastic or elastomer so that it can be conformed to the shape of the human mouth into which it is to be inserted, thus permitting deformation to the shape of the natural dentition. The sanitary oversertion sheath 14 preferably has a thickness of between 0.1 mm and 2.0 mm, although it is understood that the thickness is selected to optimize sheath strength versus sheath flexibility and light penetration.

Likewise, referring to the curing section 12 in more detail, the housing 16 is constructed and arranged as follows. The housing 16 is provided with a flat housing top 36 and a flat housing bottom 38. Two opposed, semicylindrical housing sides 40, 42 are interposed between the flat housing top 36 and bottom 38, thus defining a generally flattened columnar shape of the housing 16.

The housing 16 is provided with an insertion end 44, oriented toward the inside of the human mouth to which it is inserted, and a power receiving end 46 for receipt of the power that facilitates curing of a dental compound. The insertion end 44 is generally shaped into a bow shaped tapered contour 48. The power receiving end 46 is generally shaped into a beveled power receiving end taper 50, having a trapezoidal top taper 52 and a trapezoidal bottom taper 54, each connected on opposite sides by a pair of frustroconical side sections 56, 58. Due to the orientation of the trapezoidal tapers 52, 54 and the frustroconical side sections 56, 58, a rectangular power receiving end face 60 terminates the beveled power receiving end taper 50. The rectangular power receiving end face 60 receives positive feed 62 and negative return 64.

The housing 16 is preferably constructed of a transparent or translucent, deformable, resilient plastic or elastomer so that it can be conformed to the shape of the human mouth into which it is to be inserted, thus permitting deformation to the shape of the natural dentition.

The inner dimensions of the sanitary oversertion sheath 14 are selected so as to substantially correlate with the outer dimensions of the housing 16, allowing just enough tolerance to facilitate practicable removal and insertion of the sanitary oversertion sheath 14 and yet permit a sufficiently snug fit so as to effect retention of the sanitary oversertion sheath 14 on the housing 16. The length of the sanitary oversertion sheath 14 is selected to approximately coincide with the effective length of the curing section 12.

The housing 16 is constructed and arranged so as to be substantially sealed. The sanitary oversertion sheath 14 is constructed and arranged so as to be disposable, that is, materials are selected so as to minimize the production costs of the sanitary oversertion sheath 14.

Figure 2:
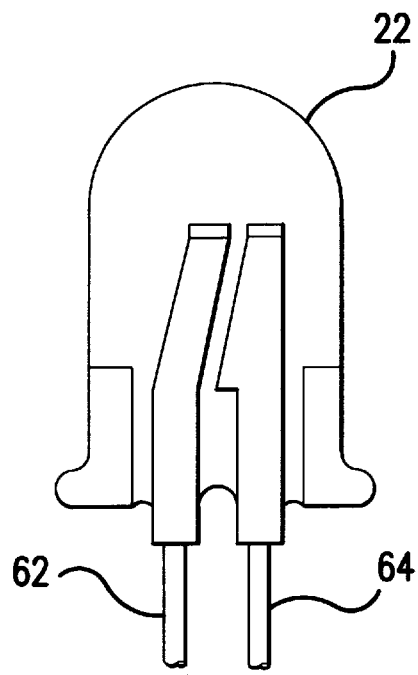
FIG. 2 illustrates a schematic view illustrating a light emitting diode as adapted for use with the light emitting diode-array light apparatus for curing adhesives, sealants and/or whitening or coloring agents used in the dentistry field.
Figure 3:
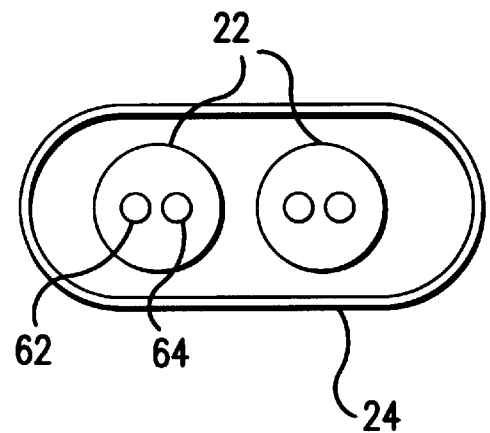
FIG. 3 illustrates a top plan view of a light emitting diode as adapted for use with the light emitting diode-array light apparatus for curing adhesives, sealants and/or whitening or coloring agents used in the dentistry field.

Referring now to FIGS. 2 and 3, LED 22 is provided a positive feed 62 and a negative return 64. In the preferred embodiment, power is supplied in the form of a 5 volt, direct current power supply from a transformer (not shown). However, it is understood that selection of the desired voltage and current type is dynamic, and that any voltage low enough to be safe but high enough to be effective may be used. Moreover, where light energy is to be used to effect curing, sufficient light energy is supplied to cure light sensitive materials, such as sealants.

Figure 4:
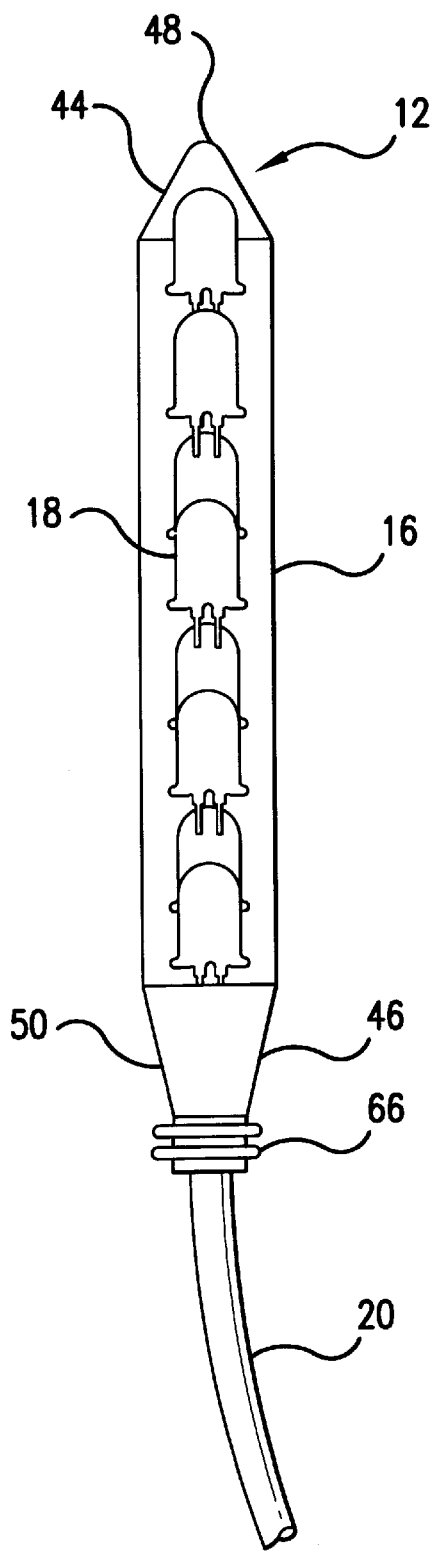
FIG. 4 illustrates a side cut-away view of a preferred embodiment of the light emitting diode-array light apparatus for curing adhesives, sealants and/or whitening or coloring agents used in the dentistry field.
Figure 5:
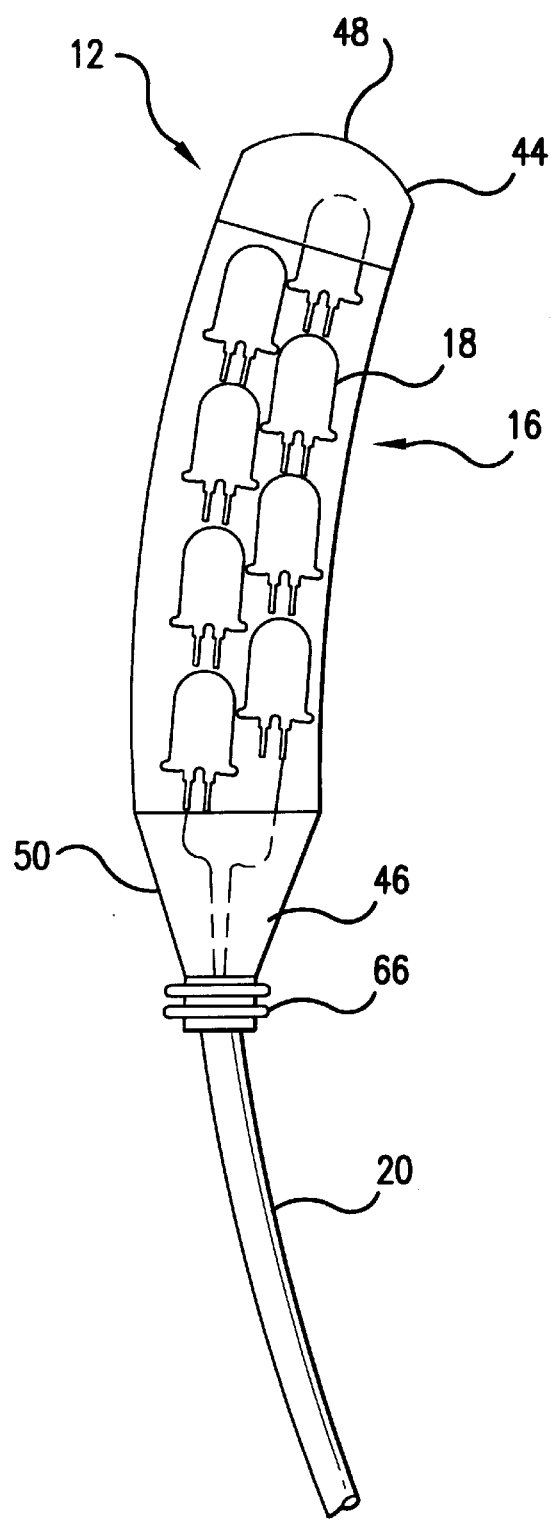
FIG. 5 illustrates a top plan cut-away view of the light emitting diode-array light apparatus for curing adhesives, sealants and/or whitening or coloring agents used in the dentistry field shown in FIG. 4.

Referring now to FIGS. 4 and 5, the housing 16 is shown in cross-sectional, cutaway view. As seen from the side, in FIG. 4, the housing 16 is provided with a flexible, corrugated, protective collar 66 that protects the power supply 20 from being broken or compromised, leading to better reliability during multiple use. The LED's 22 are imbedded in the housing 16. In the preferred embodiment, the LED array 18 is connected in parallel, although connection in serial is foreseen, as well.

Figure 6:
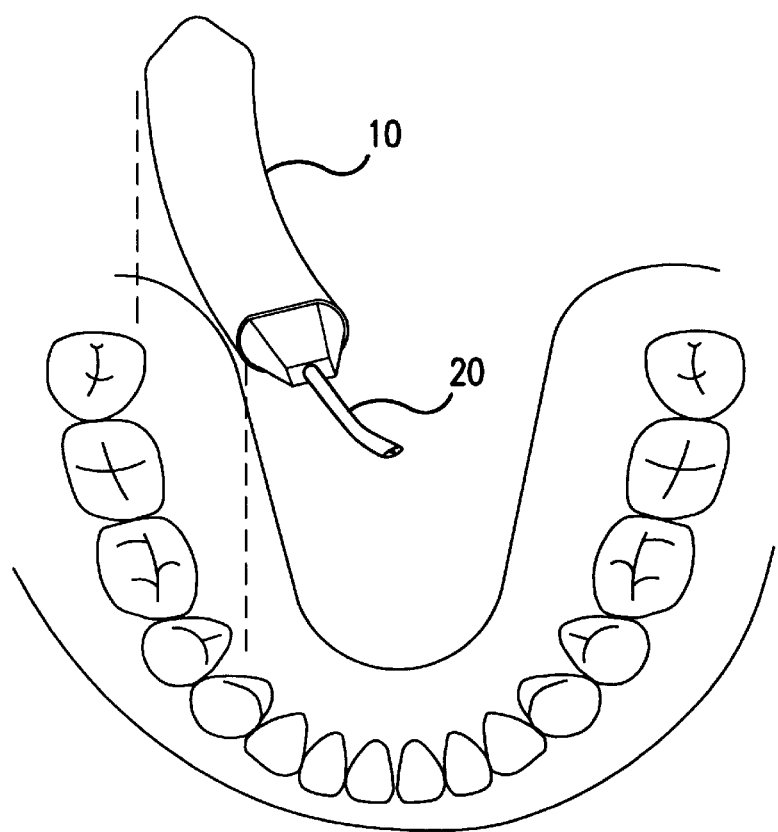
FIG. 6 illustrates a top cut-away view of the light emitting diode-array light apparatus for curing adhesives, sealants and/or whitening or coloring agents used in the dentistry field as shown in FIG. 4 as positioned in a human mouth.
Figure 7:
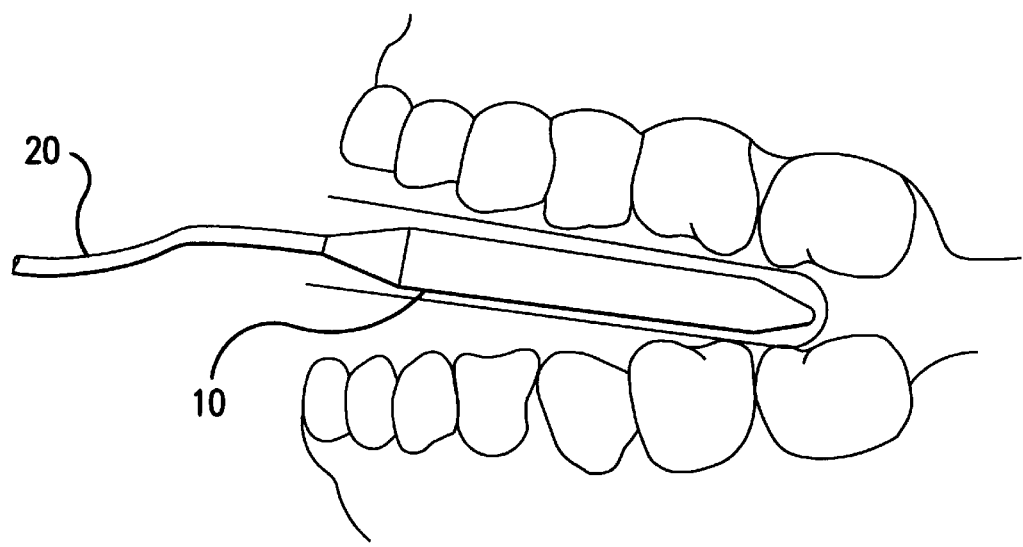
FIG. 7 illustrates a side cut-away view of the light emitting diode-array light apparatus for curing adhesives, sealants and/or whitening or coloring agents used in the dentistry field as shown in FIG. 4 as positioned in a human mouth.

As shown in FIGS. 6 and 7, the conformable, multi-tooth curing apparatus 10 is bent into the shape of natural dentition specific to the particular patient to be treated. Once adhesives, sealants or whitening agents have been inserted into the desired locations within the patient's mouth, the conformable, multi-tooth curing apparatus 10 is placed in the human mouth. Power is supplied to the LED array 18 so that curing is effected.

Figure 8:
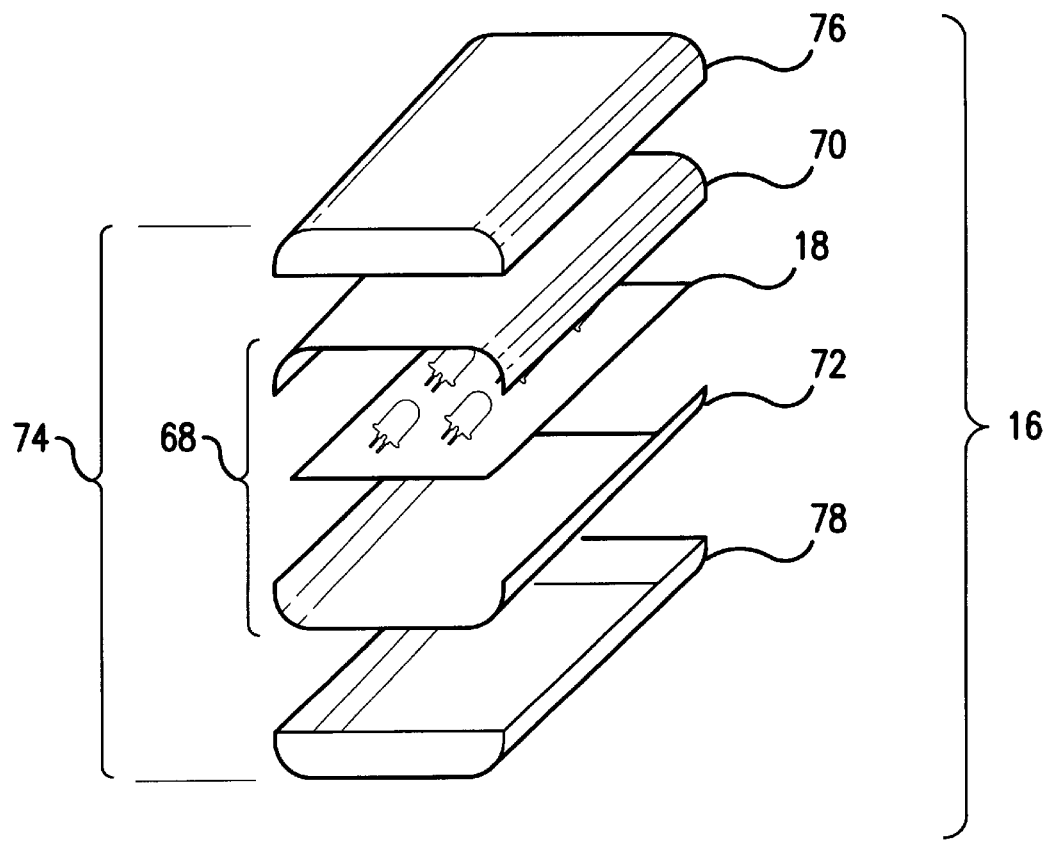
FIG. 8 illustrates an exploded, perspective view of a portion of a preferred embodiment of the apparatus.

FIG. 8 illustrates an exploded view of yet another embodiment of the housing 16. Here, the LED array 18 is contained within a diffuser grid 68 comprising two diffuser grid halves 70, 72. The diffuser grid 68 is, in turn, contained within an outer shell 74 comprising a pair of outer shell halves 76, 78.

Figure 9:
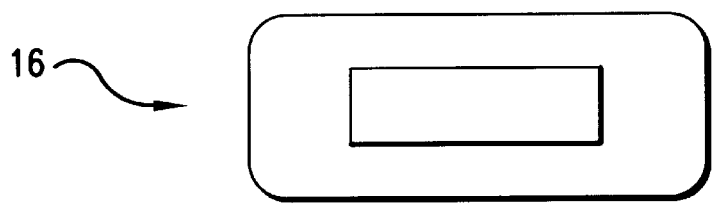
FIG. 9 illustrates a frontal plan view of the apparatus shown in FIG. 8.

FIG. 9 illustrates a front view of the housing 16 shown in FIG. 8. The housing 16 is approximately ¾ inches wide and 5/16 inches high.

FIGS. 10 through 12 illustrate additional perspective views of the preferred embodiment shown in FIG. 8. The LED array 18 is shown in FIG. 10.

FIG. 11 shows the curing section 12 from a top perspective view. FIG. 12 illustrates a side view of the curing section 12. The curing section as shown is approximately 3 inches long.

Figure 13:
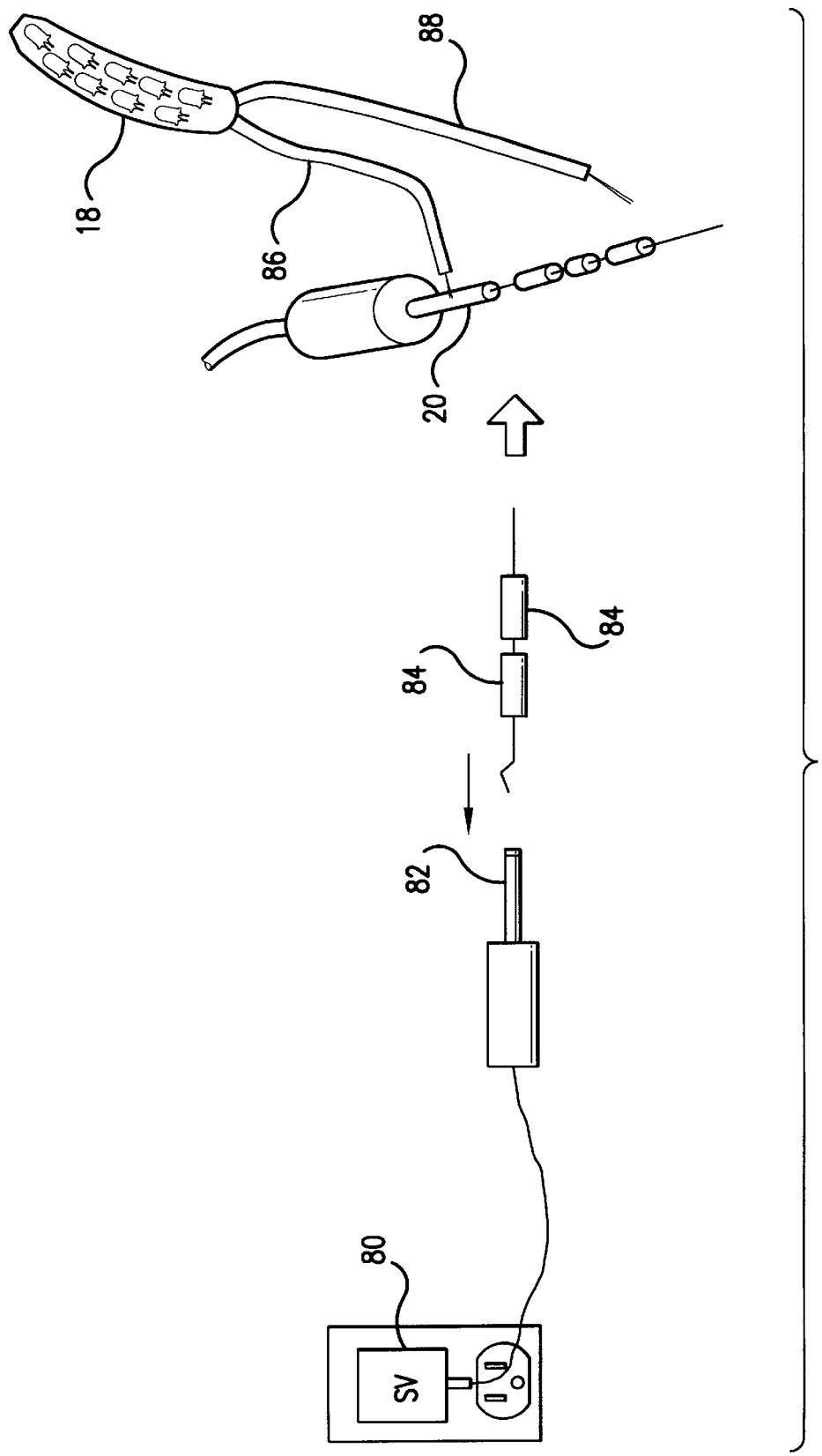
FIG. 13 illustrates a side perspective view of the light emitting diode-array light apparatus for curing adhesives, sealants and/or whitening or coloring agents used in the dentistry field as assembled for use in the field.

FIG. 13 illustrates use of the apparatus. In this particular embodiment, the transformer 80 connects to a 110 volt, AC power supply and provides a 3 volt, DC power supply to the apparatus 10. A DC power plug 82 is connected to a series of resistors 84, each having approximately 100 ohms of resistance, to provide the desired amperage. A red lead 86 and a black lead 88 are connected to the apparatus 10. By touching the leads 86, 88 to the power supply 20, electricity is conducted through the LED array 18 to effect curing of the dental compound to be cured.

Thus, the LED position and conductor arrangement, with the anode and cathode separated on opposing sides of a opto-electronic board, is illustrated. The opto-electronic board may have lens and/or light diffusing properties. As illustrated, the LED units are connected in parallel. The board is preferably constructed of a stamped or molded transparent, temperature-resistant, electrically insulating material, such as Dupont Corporation's Mylar.

The circuit pattern can be etched or otherwise embedded into the opto-electronic board. To fully encase the completed array, the board can be implanted in a mold which is then filled with a electrically neutral resin or urethane. This is then sealed within two pre-molded half sections to fully enclose the board. Additional holes may be drilled or molded in the opto-electronic board for ease in aligning the board in the casing and stabilizing its position.

The lens/casing could be molded from 94V-0 compliant polycarbonate, which would assure maximum light transmission and increased protection from ESD. Alternatively, Lexan or Lucite may also be used. Surrounding the array with a resin and mold can be accomplished by using an electrically neutral, clear, self-curing resin such as 3M Corporation's DP-270 two-component system. Another alternative could be W.R. Grace and Company's Stycast 1267 Epoxy Encapsulant, or Conap Corporation's Conathane UC53 urethane.

In an alternative embodiment, stainless steel wire is braided over each LED lead and crimped in position. Two separate housing halves were created using balsa patterns and vacuforming equipment. The optoelectronic board was placed between the halves, which were heat annealed together. The apparatus is transparent.

A device 10 for curing adhesives, sealants and/or whitening or coloring agents used in the dentistry field is therefore described. The LED array 18 is connected, preferably but not necessarily in parallel. A relatively low voltage source, such as one having about 5 volts, delivered from a transformer, powers the LED array 18. The LED array 18 is protected within a clear, a transparent and/or a translucent housing 16. The housing 18 is sealed. The housing 18 can be constructed of a solid, such as a poured resin, or can be constructed as a hollow structure.

The housing 18 has a shape with an overall curve that conforms to an approximate shape of dentition. In the preferred embodiment, the housing 18 is constructed as a flexible material, including a flexible material that has shape memory characteristics. The housing 18 is mountable within a disposable oversertion sheath 14, for sterility purposes. During use, the LED array 18 transmits light which cures the adhesives, sealants and/or whitening or coloring agents, preferably on several teeth simultaneously.

Thus, a conformable, multi-tooth light emitting diode-array light apparatus for curing adhesives, sealants and/or whitening or coloring agents used in the dentistry field is disclosed. While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. For use in a human mouth containing teeth having a specific contour, a dental curing apparatus comprising, in combination:

a curing section and an oversertion sheath;

the curing section being reusable and having an LED array contained within a housing;

the housing further having a generally flattened, elongated shape and having an insertion end oriented toward the human mouth into which the apparatus is placed and having at its opposite end a power receiving end for receiving an electrical current, the housing being sealed with respect to the LED array such that the LED array is maintained in non-contacting relation to the human mouth;

the oversertion sheath being disposable and having a generally flattened, elongated shape and having a tapered sheath end oriented toward the human mouth into which the apparatus is placed and having at its opposite end a housing receiving aperture;

the oversertion sheath being constructed and arranged so as to receive the housing, the housing being constructed and arranged so as to be insertable into the oversertion sheath; and the curing apparatus having an overall length greater than approximately one inch and being conformable to the specific contour of the teeth within the human mouth with which it is to be used, the housing further having a flat housing top and a flat housing bottom and two opposed, semicylindrical housing sides interposed between the flat housing top and flat housing bottom; whereby the housing has a generally flattened columnar shape.

2. A dental curing apparatus according to claim 1 wherein the oversertion sheath further has a flat sheath top and a flat sheath bottom, the top and bottom being joined by opposed, semicylindrical sheath sides to form a flattened tubular shape constructed and arranged to receive the curing section; the oversertion sheath having a tapered sheath end at one end and a housing receiving aperture at the opposite end.

3. A dental curing apparatus according to claim 2 wherein the housing insertion end has a generally bow shaped tapered contour, the power receiving end being beveled and having a trapezoidal top taper and a trapezoidal bottom taper, the top and bottom tapers being connected on opposite sides by a pair of opposed, frustroconical side sections, whereby the power receiving end taper terminates in a rectangular power receiving end face constructed and arranged for receiving a power supply.

4. A dental curing apparatus according to claim 3 wherein the inner dimensions of the oversertion sheath substantially correlate with the outer dimensions of the housing, thereby allowing sufficient tolerance to facilitate practicable removal and insertion of the oversertion sheath from the housing and yet also to facilitate effective retention of the oversertion sheath on the housing.

5. A dental curing apparatus according to claim 1 wherein the housing insertion end has a generally bow shaped tapered contour, the power receiving end being beveled and having a trapezoidal top taper and a trapezoidal bottom taper, the top and bottom tapers being connected on opposite sides by a pair of opposed, frustroconical side sections, whereby the power receiving end taper terminates in a rectangular power receiving end face constructed and arranged for receiving a power supply.

* * * * *